United States Patent
Hennink et al.

[11] Patent Number: 5,219,325
[45] Date of Patent: Jun. 15, 1993

[54] WOUND DRESSING AND METHOD OF PREPARING THE SAME

[75] Inventors: Wilhelmus E. Hennink, Waddinxveen; Jacobus J. Zandman, Delft; Maria E. van der Heijden-van Beek; Hendrik Teunissen, both of Weesp, all of Netherlands

[73] Assignee: Duphar International, Research B.V., Weesp, Netherlands

[21] Appl. No.: 661,238

[22] Filed: Feb. 27, 1991

[30] Foreign Application Priority Data

Mar. 2, 1990 [NL] Netherlands .............. 9000494

[51] Int. Cl.$^5$ .............................. B32B 27/00
[52] U.S. Cl. ...................... 602/41; 602/48; 602/58
[58] Field of Search .................. 604/304-307, 604/367, 20; 128/155, 156, 112.1, 113.1, 114.1; 602/41, 48, 49, 52-58; 424/449

[56] References Cited

U.S. PATENT DOCUMENTS

| | | | |
|---|---|---|---|
| 3,419,006 | 12/1968 | King | 602/48 |
| 4,552,138 | 11/1985 | Hofeditz et al. | |
| 4,556,056 | 12/1985 | Fischer et al. | |
| 4,646,730 | 3/1987 | Schonfeld et al. | |
| 4,750,482 | 6/1988 | Sieverding | 128/156 |
| 4,793,337 | 12/1988 | Freeman et al. | 602/49 |
| 4,889,530 | 12/1989 | Smith et al. | 604/304 |

FOREIGN PATENT DOCUMENTS

| | | |
|---|---|---|
| 0011471 | 5/1980 | European Pat. Off. |
| 0305052 | 3/1989 | European Pat. Off. |
| 0305770 | 3/1989 | European Pat. Off. |
| 2542201 | 9/1984 | France |
| 2596404 | 10/1987 | France |

*Primary Examiner*—Randall L. Green
*Assistant Examiner*—Gina M. Gualtieri
*Attorney, Agent, or Firm*—Stevens, Davis, Miller & Mosher

[57] ABSTRACT

The invention relates to a wound dresssing comprising (1) a lower layer of a hydrogel of a polymer crosslinked under the influence of electron beam (E.B.) radiation, to which optionally one or more medicinal and-/or antibacterial agents and/or one or more auxiliary substances have been added, and (2) a polymeric top layer, in which the top layer consists at least substantially of an elastomer selected from the group consisting of a silicone rubber, a polyetherpolyurethane copolymer, a polyester-polyurethane copolymer, a polyetherpolyester copolymer and an optionally modified block copolymer based on suitable vinyl monomers, and that a fibrous layer is provided between the lower layer and the top layer for bonding the two layers together.

The invention further relates to a method of preparing said wound dressing.

9 Claims, 1 Drawing Sheet

WOUND DRESSING AND METHOD OF PREPARING THE SAME

BACKGROUND OF THE INVENTION

The invention relates to a wound dressing comprising (1) a lower layer of a hydrogel of a polymer cross-linked under the influence of electron beam (E.B.) radiation, to which optionally one or more medicinal and-/or antibacterial agents and/or one or more auxiliary substances have been added, and (2) a polymeric top layer A wound dressing is to be understood to mean herein not only a cover of a wound, but also a cover of an undamaged skin, for example, when protection hereof is desired from medical or cosmetic considerations.

Such a wound dressing is known from the literature, for example, from European Patent Application 305770 and from U.S. Pat. No. 4,646,730. In these patent publications a cross-linked polyvinyl pyrrolidone (PVP) gel prepared by exposing a PVP solution in water to E.B.-radiation is used as a lower layer to be provided directly on the wound. Various medicaments, for example, silver sulfadiazine, a known antibacterial agent, may be added to the said lower layer. In the United States Patent Specification mentioned hereinbefore it is suggested to add a stabiliser to the dispersion of silver sulfadiazine in the aqueous PVP solution so as to obtain in the E.B. radiation a gel having a uniform colour. The resulting hydrogel is provided on a suitable carrier, for example, a non-woven and/or a polyethylene sheet. Such a polymeric top layer is necessary to support the lower layer. However, polyethylene is not a suitable material to serve as a top layer for wound dressing because it is not or hardly permeable to gas and vapour. As a matter of fact, the following requirements must be imposed upon polymeric sheet materials for wound dressing: (1) they must constitute a barrier to penetrating microorganisms, (2) they must ensure a sufficient exchange of $O_2$ and $CO_2$ to stimulate the healing process, and (3) they must be sufficiently permeable to moisture vapour.

Suitable polymer sheet materials for wound dressing are described in European Patent Application 11471. Such materials are manufactured, for example, from polyether-polyurethane copolymer and have a sufficient elasticity to adapt to the skin in the form of a sheet or film. Moreover, such materials are particularly suitable for wound dressing because they combine a good moisture vapour permeability with the property of barring microorganisms. The polymer sheet to be used as a wound dressing in the last-mentioned European Patent Application comprises on one side an adhesive layer in which an antibacterial agent, for example, silver sulfadiazine, may be incorporated.

BRIEF SUMMARY OF THE INVENTION

It is the object of the present invention to provide a wound dressing of the type mentioned in the opening paragraph, i.e. having a lower layer of a hydrogel of a polymer cross-linked under the influence of E.B.-radiation, which has a polymeric top layer with the favourable properties of the sheet material described in European Patent Application 11471. It has been found that adhesive bonding of the two layers together does not provide a good solution. Most of the adhesives that have been tested do not provide a satisfactory bonding between the hydrogel layer on the one hand and the used polymeric top layer on the other hand.

A satisfactory bonding between the layers could be achieved only by using a cyanoacrylate adhesive. However, this adhesive bond had unsatisfactory elasticity, while moreover the polymeric top layer used started to show cracks at the areas where the adhesive had been provided.

FIG. 1 shows a partial cross section of a wound dressing of the present invention, in which 10 indicates the wound dressing, 11 indicates the polymeric top layer, 12 indicates the fibrous layer, and 13 indicates the lower layer of a hydrogel of a polymer cross-linked under the influence of electron beam radiation.

The object mentioned hereinbefore could be achieved by means of a wound dressing which according to the invention is characterised:

by the use of a top layer which consists at least substantially of an elastomer selected from the group consisting of a silicone rubber, a polyether-polyurethane copolymer, a polyester-polyurethane copolymer, a polyether-polyester copolymer, and an optionally modified block copolymer based on suitable vinyl monomers, such as styrene, butadiene, ethylene, butylene and/or vinyl acetate; and by providing a fibrous layer between the lower layer and the top layer for bonding the two layers together.

It has been found surprisingly that an excellent bonding between the lower layer and the elastomeric top layer can be obtained by using a suitable fibrous layer which is present at the interface of the two layers. The fibrous layer may be a layer of incoherent fibres or a layer of coherent fibres which is usually referred to as a textile layer. An elastic textile layer is preferably used, preferably a fabric (knitting) of a polyester, a polyamide or a polyurethane.

One or more medicinal and/or antibacterial agents may optionally be incorporated in the lower layer. In addition to the silver sulfadiazine already mentioned hereinbefore, the following antibacterial agents are to be considered:

(i) organic compounds of antibacterial metal ions, such as copper, mercury or silver; (ii) topical antibiotics, such as gentamycin, neomycin, soframycin, bacitracin and polymyxin; (iii) antibacterial agents, such as chlorohexidine and salts thereof; (iv) quaternary ammonium compounds, such as cetrimide, domiphenbromide and polymeric quaternary ammonium compounds; and (v) iodophoric compounds, such as polyvinyl pyrrolidone-iodine.

Suitable auxiliary substances which may be incorporated in the lower layer are—in addition to the stabilisers already mentioned hereinbefore—physiologically acceptable dyes, pigments, flavourings (fragrancies), plasticisers antioxidants, fillers in the form of fibres or powders and preservatives. Such auxiliary substances, notably dyes, pigments and optionally fillers, may also be incorporated in the top layer, if so desired.

Various hydrogel-forming polymers are suitable for being cross-linked under the influence of E.B.-radiation. In addition to the already mentioned polyvinyl pyrrolidone, suitable polymers to be cross-linked are: polyvinyl alcohol, polyether, polyhydroxyethyl methacrylate, hydroxyethyl cellulose, hydroxypropyl cellulose, hydroxypropyl methylcellulose, polysaccharide, alginate, vinylalcohol-vinylfluoride copolymer and mixtures of these polymers.

The lower layer must satisfy stringent requirements because direct contact with the wound takes place. In addition to the requirements already described for the top layer, such as moisture vapour permeability and elasticity/flexibility, the lower layer must preferably also provide a contribution to moisture absorption and moisture transport, it must not adhere to the wound, and it must not promote tissue growth in the lower layer itself. When the last-mentioned requirements are not satisfied, the healing process is disturbed when the dressing is removed from the wound. Naturally, the lower layer may not deliver any substances which are detrimental to the healing process.

In connection with the requirements imposed hereinbefore and the extraordinary suitability for forming a hydrogel under the influence of E.B.-radiation, a polyvinyl alcohol is to be preferred for the lower layer. The cross-linking of a polyvinyl alcohol under the influence of formaldehyde or glutaric aldehyde, as described in U.S. patent Specification 4,552,138 and French Patent Application 2,596,404, respectively, has considerable disadvantages compared with the cross-linking under E.B.-radiation. In a simple treatment and under very mild conditions the polyvinyl alcohol can be cross-linked under the influence of E.B.-radiation to the desired cross-linking degree, while the final product cannot be contaminated by detrimental substances, such as formaldehyde or glutaric aldehyde. It is known that a substance such as glutaric aldehyde, even in a concentration of 3 ppm, already disturbs the healing process of a wound substantially entirely. As a result of the comparatively mild conditions in which the cross-linking process according to the invention takes place—i.e. under E.B.-radiation - sensitive medicinal and antibacterial agents can also remain better intact during the said treatment.

A silicone rubber which has also been cross-linked under the influence of E.B.-radiation has been found to be best suitable as a top layer. Since non-cross-linked silicone rubber or silicone resin can be readily cross-linked under the influence of E.B.-radiation, the degree of cross-linking and hence the properties of the cross-linked product can be adjusted at will by applying a given dose of radiation. Moreover, silicone rubber as a final product of the E.B.-curing excellently satisfies the requirements mentioned hereinbefore imposed upon the top layer, an extra advantage being that the product is not contaminated with remainders of toxic initiator necessary in the conventional thermal curing.

DETAILED DESCRIPTION OF THE INVENTION

Figure 1:
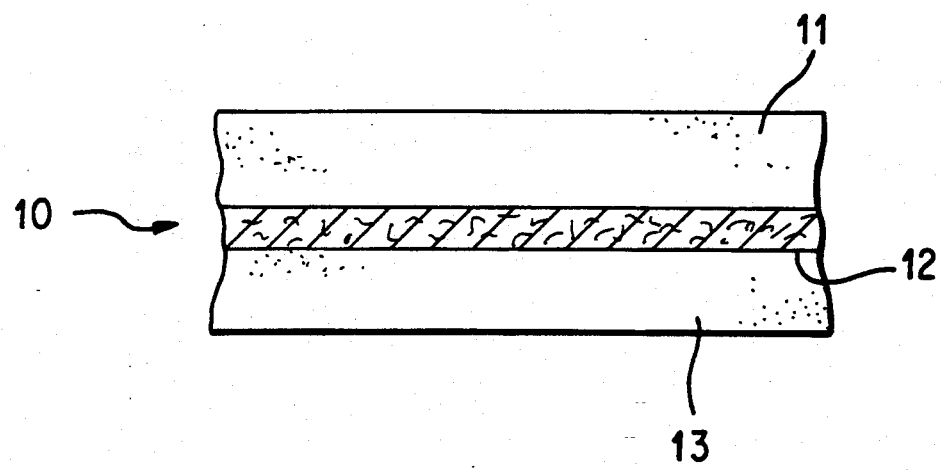

Therefore, a wound dressing is to be preferred which is characterised according to the invention in that the lower layer consists at least substantially of a hydrogel of a polyvinyl alcohol crosslinked under the influence of E.B.-radiation to which optionally one or more medicinal and/or antibacterial agents, in particular silver sulfadiazine, and/or one or more auxiliary substances have been added, in that the top layer consists of a silicone rubber which has also been cross-linked under the influence of E.B.-radiation, and in that the fibrous layer for the mutual bonding of the two layers is an elastic textile layer, preferably an elastic fabric (knitting).

The invention is not restricted to a wound dressing but also extends to a method of preparing the same. As a matter of fact, the method of preparing the wound dressing is of direct influence on the mutual bonding of the lower layer to the top layer. In order to produce an optimum bonding, the method according to the invention of preparing a wound dressing can be carried out as follows:

An elastomer which has not yet been cross-linked or which is insufficiently cross-linked and which has a suitable viscosity is selected as the elastomer for the top layer. The elastomer is then provided on the surface of a suitable substrate, for example, an inert polymer sheet, in a layer thickness which is desired for the top layer, and, if desired, slightly cross-linked to the desired viscosity under the influence of E.B.-radiation. The fibrous layer, preferably the elastic textile layer, is then provided on the layer of not yet or incompletely cross-linked elastomer, the fibrous layer penetrating slightly into the viscous elastomer layer. Two possibilities may then be chosen, depending on the materials to be cured and/or the power of the radiation source. The elastomeric top layer with the fibrous layer may first be further cured by means of E.B.-radiation and the lower layer may then be provided, or the lower layer may be provided on the elastomeric top layer comprising the fibrous layer without applying interim curing. The lower layer is bonded to the top layer comprising the fibrous layer by successively providing on the fibrous layer a layer of the hydrogel-forming solution of the polymer to be cross-linked in water, to which solution, if desired, one or more medicinal and/or antibacterial agents and/or one or more auxiliary substances have been added, and exposing the resulting laminated product to E.B.-radiation. Depending on the power of the E.B. apparatus and on the viscosity of the hydrogel-forming solution, the solution of the polymer to be cross-linked may be provided directly in the desired layer thickness and be subjected to E.B.-radiation, or may be exposed to radiation in several thin layers until the desired layer thickness has been reached. An elastomer which is excellently suitable for the above preferred method is a silicone rubber, while polyvinyl alcohol is to be preferred as a hydrogel to be used as a lower layer as regards its behaviour under E.B.-radiation and its favourable properties mentioned hereinbefore.

In principle, the method of preparing the wound dressing according to the invention may also be carried out in the reverse sequence. In that case, first a layer of the hydrogel-forming solution of the polymer to be cross-linked in water is hence provided on a substrate suitable for that purpose, is slightly cured to a suitable viscosity by means of E.B.-radiation, is provided with a fibrous layer, preferably an elastic textile layer, and is finally—with or without interim curing—coated with the elastomeric top layer, after which the assembly is further cured by means of E.B.-radiation to form the ready wound dressing.

Optionally, the inert polymer sheet to be used as substrate may in this phase of the production of the wound dressing be removed; however, the polymer sheet may also be included in the package. Finally, the E.B.-radiation may successfully be used to sterilise the finished final product, namely the wound dressing prepared in the above-described manner. For that purpose the resulting wound dressing in a sterile sealing package is exposed to E.B.-radiation.

The invention will now be described in greater detail with reference to the ensuing specific example.

EXAMPLE

Preparation of a Wound Dressing

Polyvinyl alcohol (PVA) (reg.trademark Mowiol 66-100) is washed with water to remove any methanol and sodium acetate. The cleaned PVA is then dissolved in water while stirring at elevated temperature in a concentration of 12% w/w, after which silver sulfadiazine is added as an antibacterial agent in such a quantity that a final concentration of 1% w/w calculated on the PVA solution is reached.

Silicone resin (trade-indication MDX4-4210) is provided on a polymer sheet as a substrate having a smooth surface, and spread to a thickness of 24 /µm. Suitable substrates are polyethylene sheets, polypropylene sheets and polyester sheets; polished metal sheets may also be used for this purpose. The resin layer provided on the sheet is now passed through an E.B.-apparatus and irradiated therein with a dose of 3 Mrad. A polyester fabric (knitting; type 80022 of Bondwick) is used as a textile layer. The fabric is provided on the resin layer which is still slightly viscous and is carefully pressed-on. The assembly is passed through the E.B.-apparatus once more and irradiated therein with a dose of 15 Mrad.

The above-described PVA-solution is then provided on the fabric and spread to a thickness of 100 /µm. After E.B.-radiation with a dose of 15 Mrad another 100 /µm thick layer of PVA-solution is provided and irradiated with 15 Mrad.

The resulting wound dressing is then removed from the substrate and, after covering with a polypropylene sheet packaged in a metallised foil. The packaged final product is passed two times through the E.B.-apparatus for sterilisation, both sides being radiated with a dose of 3 Mrad.

Properties of the Resulting Wound Dressing (1) Moisture vapour Permeability (Water Vapour Permeability)

The moisture vapour permeability of a wound dressing obtained as described hereinbefore is determined by punching a circular piece having a diameter of 8.5 cm and providing it on the edge of an aluminium tray with the PVA gel (lower layer) lowermost. The edge of the tray is made watertight by means of a wax which is impermeable to water vapour and the tray is filled with a physiological saline solution (0.9% NaCl w/w). The tray is placed upside down in an oven at 37° C., the PVA-layer of the wound dressing hence being in direct contact with the physiological saline solution. The contact area between liquid and wound dressing is 50 cm$^2$. By placing a saturated solution of magnesium nitrate in the oven it is ensured that the relative humidity in the oven is 50%. By determining the weight of the tray with liquid at given intervals, the decrease in weight in time and hence the moisture vapour permeability can be determined. The moisture vapour permeability of a few commercially available wound dressings has also been determined, namely of Bioclusive (reg. Trademark: a polyurethane wound dressing comprising an adhesive layer) and Opsite (reg. trademark). For two wound dressings according to the invention produced in the above-described manner moisture vapour permeabilities of 1503 and 1755 g/m$^2$.24h are found. For the comparative products Opsite and Bioclusive the following values for the moisture vapour permeability are found: 481 and 337 g/m$^2$/.24 h, respectively.

So the wound dressing according to the invention has a high moisture vapour permeability compared with the commercially available types of wound dressing. This is a favourable property, in particular when applied to strongly exuding wounds.

(2) Extensibility

The wound dressing according to the invention is tested for extensibility by elongating samples, 5 cm long and 1 cm wide, in the transversal direction or in the longitudinal direction to fracture. The percentage elongation to fracture upon loading in the transversal direction is 147% at a force of 28N upon loading in the longitudinal direction 297% at a force of 17N.

So the resulting wound dressing according to the invention has a good extensibility and is hence very suitable for wound dressing. During these elongation tests the layers remain firmly bonded together until the instant of fracture.

(3) Effectiveness Against Bacteria

As already stated hereinbefore, a wound dressing according to the invention is prepared, in which 1% (w/w) of silver sulfadiazine is incorporated in the PVA layer. The effectiveness of the wound dressing against various bacteria (microbial pathogens) is determined as follows.

Cultures of *E. coli* in a suitable growth medium are shaken at 37° C. in the presence of a sample of the wound dressing according to the invention described hereinbefore. The effect of the wound dressing on the viability of the microorganisms is determined by determining the number of colony-forming units ("cfu's") per ml. This is performed by taking samples at various time intervals, incubating them after dilution on agar plates, and counting the number of cfu's. In the wound dressing according to the invention the number of cfu's/ml was reduced to less than 0.01% within 3 hours. For example, incubation of a 50 ml E. coli culture with 25 cm$^2$ of wound dressing provides a reduction in the number of cfu's/ml from 10$^8$ (t=0) to less than 5 × 10$^3$ (t=3h) within 3 hours. It has moreover been found in this experiment that complete sterilisation is effected within 24 hours after the addition of the wound dressing to the culture.

It has moreover been found that after pre-incubation of the wound dressing in growth medium for 48 hours, succeeded by transfer of the wound dressing to an *E. coli* culture, the wound dressing still shows effectiveness against *E. coli*.

This means that even after 48 hours of incubation active substance is still released from the wound dressing.

Corresponding results are obtained when *P.aeruoinosa* is used as a test organism instead of *E. coli*.

We claim:

1. A wound dressing comprising: a lower layer of a hydrogel of a polymer cross-linked under the influence of electron beam radiation; a polymeric top layer comprising at least substantially an elastomer selected form the group consisting of a silicone rubber, a polyether-polyurethane copolymer, a polyester-polyurethane copolymer, a polyether-polyester copolymer and an optionally modified block copolymer based on suitable vinyl monomers; and a fibrous layer provided between the lower layer and the top layer to bond the two layers together;

said fibrous layer being an elastic textile layer selected from the group consisting of a polyester fabric, a polyamide fabric and a polyurethane fabric.

2. A wound dressing as claimed in claim 1, wherein the lower layer comprising at least substantially a hydrogel of a polyvinyl alcohol cross-linked under the influence of electron beam radiation.

3. A wound dressing as claimed in claim 1, wherein the top layer consists of a silicone rubber which has also been cross-linked under the influence of electron beam radiation.

4. A wound dressing as claimed in claim 1, wherein silver sulfadiazine, alone or in combination with at least one additional substance selected from the group consisting of medicinal agents, antibacterial agents and auxiliary substances, is added to the lower layer.

5. A wound dressing as claimed in claim 1, wherein at least one substance selected from the group consisting of medicinal agents, antibacterial agents and auxiliary substances is added into the lower layer.

6. A wound dressing as claimed in claim 1, wherein at least one agent selected for the group consisting of silver sulfadiazine, organic compounds of antibacterial metal ions, chlorohexidine and salts thereof, quaternary ammonium compounds and iodophoric compounds is added into the lower layer.

7. A wound dressing comprising: a lower layer comprising at least substantially a hydrogel of a polyvinyl alcohol cross-linked under the influence of electron beam radiation; a polymeric top layer comprising at least substantially a silicone rubber which has also been cross-linked under the influence of electron beam radiation; and an elastic textile layer provided between the lower layer and the top layer to bond the two layers together;
 wherein the elastic textile layer is selected from the group consisting of a polyester fabric, a polyamide fabric and a polyurethane fabric.

8. A wound dressing as claimed in claim 7, wherein at least one substance selected from the group consisting of silver sulfadiazine, other medicinal agents, other antibacterial agents and auxiliary substances is added into the lower layer.

9. A wound dressing as claimed in claim 7, wherein silver sulfadiazine is added into the lower layer.

* * * * *